United States Patent [19]

Koziol et al.

[11] Patent Number: 4,581,031

[45] Date of Patent: Apr. 8, 1986

[54] PRISMATIC INTRAOCULAR LENS

[76] Inventors: Jeffrey E. Koziol, 601 W. Central, Mount Prospect, Ill. 60056; Gholam A. Peyman, 535 N. Michigan Ave., Chicago, Ill. 60611

[21] Appl. No.: 623,408

[22] Filed: Jun. 22, 1984

[51] Int. Cl.$^4$ ............................................. A61F 2/16
[52] U.S. Cl. ...................................... 623/6; 351/170; 351/175
[58] Field of Search ............... 3/13, 1; 351/167, 170, 351/175

[56] References Cited

U.S. PATENT DOCUMENTS

| | | | |
|---|---|---|---|
| 815,648 | 3/1906 | Slagle | 351/170 |
| 1,659,197 | 2/1928 | Glancy | 351/175 |
| 3,245,745 | 4/1966 | Hancock | 351/167 |
| 4,010,496 | 3/1977 | Neefe | 3/13 |
| 4,242,760 | 1/1981 | Rainin | 3/13 |
| 4,251,887 | 2/1981 | Anis | 3/13 |
| 4,257,130 | 3/1981 | Bayers | 3/13 |
| 4,277,851 | 7/1981 | Choyce | 3/13 |
| 4,277,852 | 7/1981 | Poler | 3/13 |
| 4,402,579 | 9/1983 | Poler | 3/13 X |
| 4,418,431 | 12/1983 | Feaster | 3/13 |

OTHER PUBLICATIONS

New from Cilco... The Single-Piece Perspex Posterior Chamber Lens (Advertisement), Cilco, Inc., 1616 13th Ave., Huntington, West VA 25701, 2 pages, Mar. 1981.
The Simcoe Anterior Chamber Lens from Cilco (Advertisement) Cilco, Inc., 4 pages, Mar. 1983.

Primary Examiner—Ronald L. Frinks
Attorney, Agent, or Firm—Roylance, Abrams, Berdo & Goodman

[57] ABSTRACT

An intraocular lens including a convex portion and a prismatic portion for use with patients having macular degeneration of the retina. The lens is to be implanted in the eye, after removal of the natural lens, to direct rays of light away from the diseased center of the retina and focus them on an undiseased area of the retina, thereby improving sight.

11 Claims, 6 Drawing Figures

PRISMATIC INTRAOCULAR LENS

FIELD OF THE INVENTION

This invention relates to intraocular lenses to be implanted in the eye upon removal of the natural lens for treatment of macular degeneration of the eye. The intraocular lens includes a prismatic portion to direct rays of light away from the diseased center of the retina and a convex portion to focus them on an undiseased area of the retina, thereby improving sight.

BACKGROUND OF THE INVENTION

A disease of the eye known as macular degeneration has become one of the leading causes of blindness in adults. This disease affects the central retinal area known as the macula which affords acute vision and receives light focused by the cornea and lens. This disease can lead to a gradual or sudden loss of vision to the level of 20/200 or less. Commonly, loss of vision only affects the central retinal area of about 0.25 to 4 square millimeters and does not usually progress beyond this area, thereby leaving 95–99% of the retina unaffected. Thus, reading and driving vision can be lost but peripheral vision remains intact.

Most cases of macular degeneration are untreatable, although laser photocoagulation has been proven to be of some benefit in certain instances. Adding prisms to a patient's glasses, who has this macular degeneration disease, also is ineffective because two things happen. First, the eye moves during normal vision while eyeglasses remain stationary. This causes distortion of the visual image as the eye moves back and forth relative to the surface of a fixed prism in the glasses. This distortion is disabling to clear sight and increases as the power of the prism increases. Secondly, if light is redirected by prismatic glasses, in order to strike the paracentral area of the retina, it must pass outside the nodal point of the eye and therefore create oblique astigmatism. This would create distortion of the image. Thus, such prisms in eyeglasses do not provide a solution to the problem.

An example of eyeglasses having prisms therein is disclosed in U.S. Pat. No. 3,245,745 to Hancock. Examples of typical intraocular lenses are described in the following U.S. Pat. Nos.: 4,010,496 to Neefe; 4,242,760 to Rainin; 4,251,887 to Anis; 4,257,130 to Bayers; 4,277,851 to Choyce; and 4,277,852 to Poler.

Thus, there is a continuing need for providing a viable treatment for macular degeneration.

SUMMARY

Accordingly, a primary object of the invention is to provide a treatment for macular degeneration in the human eye comprising an intraocular lens having a prismatic portion for redirecting light rays away from the diseased macula as well as a convex portion for focusing these light rays.

Another object of the invention is to provide such a lens that can be placed in the anterior or posterior chamber of the eye after removal of the natural lens.

Another object of the invention is to provide such a lens having a prismatic portion and a convex portion which are integrally formed as one piece.

The foregoing objects are basically attained by providing an intraocular lens adapted to be implanted in the eye comprising a lens portion having a first portion and a second portion, the first portion including means for focusing light entering the eye, the second portion including prism means for deflecting light entering the eye away from the center of the retina; and means, coupled to the lens portion, for supporting the lens portion in the eye.

Other objects, advantages and salient features of the present invention will become apparent from the following detailed description, which, taken in conjunction with the annexed drawings, discloses a preferred embodiment of the invention.

DRAWINGS

Referring now to the drawings which form a part of this original disclosure:

DETAILED DESCRIPTION OF THE INVENTION

Figure 1:
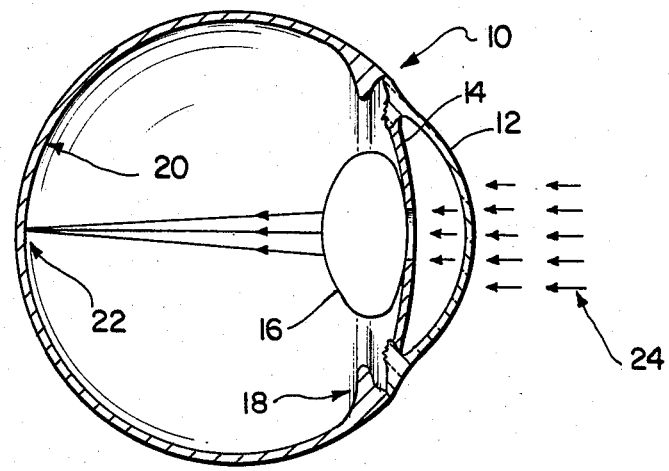
FIG. 1 is a side elevational view in longitudinal section of a schematic representation of a human eye including a natural lens.

As seen in FIG. 1, an eye 10 is shown including the cornea 12, iris 14, lens 16, the ciliary sulcus 18 adjacent the lens, the retina 20 and the macula 22.

As illustrated in FIG. 1, the macula 22 is located at the center of the retina 20 and is responsible for providing acute vision, such as that necessary for driving or reading. As seen in FIG. 1, light rays 24 are focused directly on the macula 22 by means of the cornea and the lens. The cornea has on the average 40 diopters of plus power and the lens has 20 diopters of plus power. This is equivalent to a very strong lens of 60 diopters. Thus, light rays 24 striking this system comprising the cornea and the lens substantially perpendicular to the eye are focused clearly on the macula 22 and provide acute vision, while light rays striking this system obliquely are unfocused and provide peripheral, less acute vision. However, when macular degeneration results, acute vision is thereby lost.

Figure 2:
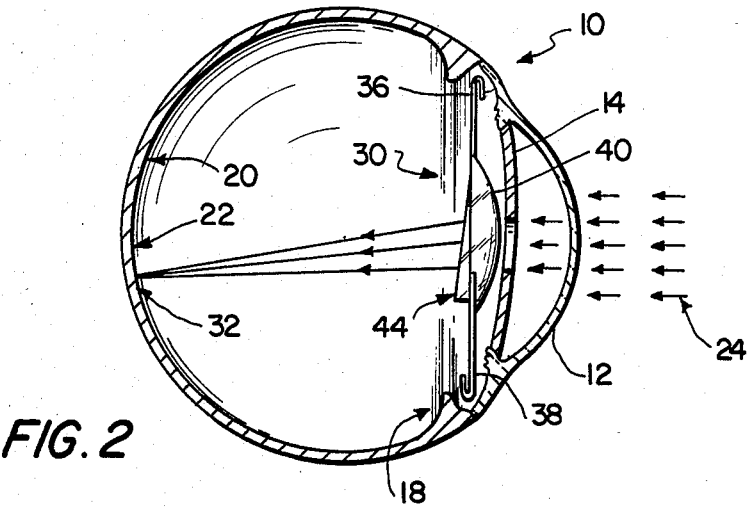
FIG. 2 is a side elevational view in longitudinal section similar to that shown in FIG. 1 except that the natural lens has been removed and the intraocular lens in accordance with the present invention has been implanted.
Figure 3:
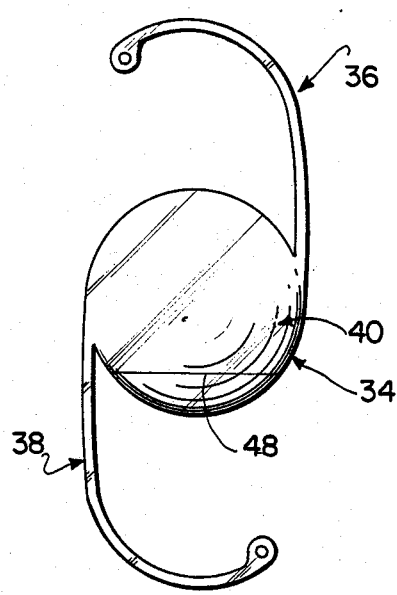
FIG. 3 is a front elevational view of the intraocular lens in accordance with the invention.
Figure 4:
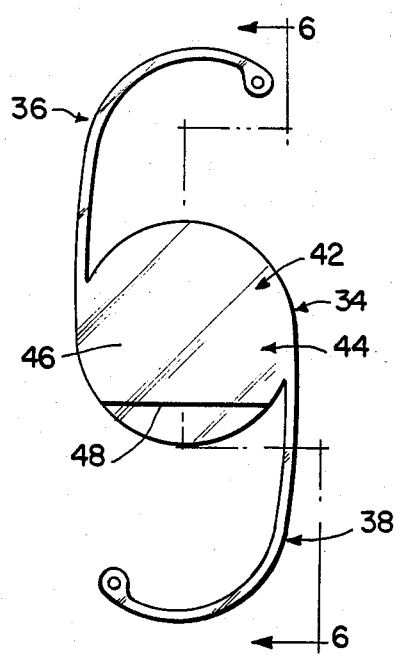
FIG. 4 is a rear elevational view of the intraocular lens shown in FIG. 3.
Figure 5:
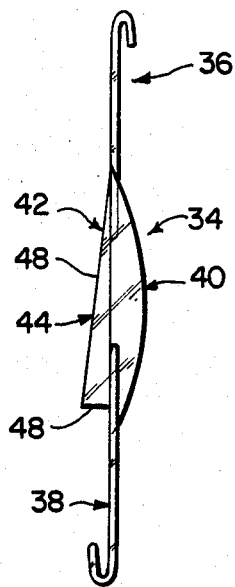
FIG. 5 is a left side elevational view of the intraocular lens shown in FIGS. 3 and 4.
Figure 6:
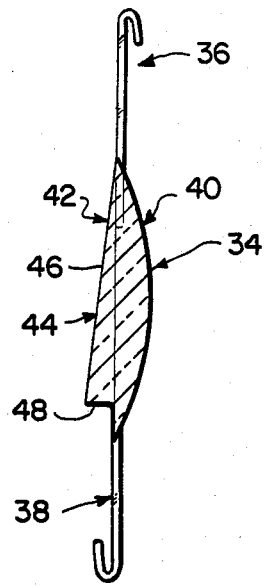
FIG. 6 is a left side elevational view in longitudinal section taken along line 6—6 in FIG. 4 of the intraocular lens.

Accordingly, the present invention as seen in FIG. 2 comprises replacing the natural lens 16 with the intraocular lens 30 in accordance with the invention so that light rays 24 are deflected away from the diseased macula 22 and are focused on an undiseased area 32 of the retina.

As seen in FIGS. 2–6, the intraocular lens 30 comprises a lens portion 34 and a pair of haptic supports 36 and 38 integrally extending from the lens portion. These supports do not have to be integrally formed with the lens portion and can be coupled thereto in any suitable fashion, as long as they support the lens portion substantially centrally of the iris 14.

The lens portion 34 can be ground or molded from suitable optical material such as optical glass or polymeric material. This lens portion comprises a first portion 40 which has a convex outer surface for focusing the light rays, and a second portion 42 including a prism 44. The prism is integrally formed with the second portion 42, which is in turn integrally formed with the first portion 40. The prism 44 includes a first planar face 46 which is at an acute angle to the central longitudinal axis passing through the lens portion and a second planar face 48 which is parallel to that axis. The outer periphery of lens portion 34 is preferably circular.

In use, the intraocular lens 30 is implanted in the eye 10 once the natural lens 16 is removed, with the supports 36 and 38 being located in the ciliary sulcus 18 to position the lens portion 34 adjacent and behind the opening in the iris 14. In this position, as seen in FIG. 2, the light rays 24 passing through the cornea 12 and the iris 14, strike the convex first portion 40 of the intraocular lens and are focused. These focused rays then exit through the prism 44 on the second portion of the lens 30 and are deflected away from the diseased macula 22 towards and against the undiseased, paracentral retinal area 32. Thus, the patient's eyesight acuity is increased. In this regard, visual acuity of the paracentral retina has been estimated to be between 20/50 and 20/200 and thus redirected and refocused light on this area will improve vision over the 20/200 experienced by those having macular degeneration. Moreover, there is evidence that paracentral retina visual function improves as this area is visually stimulated. While the lens 30 is shown in FIG. 2 positioned in the posterior chamber of the eye, it could be positioned completely in the anterior chamber.

As an example, it is contemplated that a five diopter prism incorporated in lens 30 and placed in the posterior chamber will focus light about 1 mm. away from the original focal point at the macula.

In order to deflect the light rays radially further away or closer to the diseased macula 22, the longitudinal thickness, i.e., the power, of the prism 44 can be modified before implantation, depending upon the extent of macular degeneration. In this regard, the area of the retina that is affected by macular degeneration can be measured by photography and visual field testing prior to surgery. The amount of prismatic deflection necessary to move a focused image outside the diseased, abnormal area can be then determined and incorporated into the intraocular lens. In addition, the position of the focused light rays from the intraocular lens 30 can be varied circumferentially relative to the macula by rotating the prism and convex portions relative to the supports before surgery or by rotating these portions relative to the eye after implantation.

While one advantageous embodiment has been chosen to illustrate the invention, it will be understood by those skilled in the art that various changes and modifications can be made therein without departing from the scope of the invention as defined in the appended claims. For example, rather than forming the first and second portions 40 and 42 integrally as one piece, they could be formed separately and then rigidly coupled together. In addition, rather than having the first portion 40 facing outwardly of the eye and the second portion 42 facing inwardly as shown in FIG. 2, the position of these portions can be reversed so that the first portion faces inwardly and the second portion faces outwardly.

What is claimed is:

1. An intraocular lens adapted to be implanted in the eye comprising:
   a lens portion having a first portion and a second portion,
   said first portion including means for focusing light entering the eye,
   said second portion including prism means for deflecting light entering the eye away from the center of the retina; and
   means, coupled to said lens portion, for supporting said lens portion in the eye.

2. An intraocular lens according to claim 1, wherein said prism means is integrally formed with said second portion.

3. An intraocular lens according to claim 2, wherein said second portion and said first portion are integrally formed.

4. An intraocular lens according to claim 1, wherein said second portion and said first portion are integrally formed.

5. An intraocular lens according to claim 1, wherein said means for focusing comprises a convex surface.

6. An intraocular lens according to claim 1, wherein said lens portion has a central, longitudinal axis, and said prism means comprises a first planar face extending at an acute angle to said longitudinal axis.

7. An intraocular lens according to claim 6, wherein said prism means further comprises a second planar face extending parallel to said longitudinal axis.

8. An intraocular lens according to claim 1, wherein said lens portion has a substantially circular outer periphery.

9. An intraocular lens according to claim 1, wherein said lens portion is formed of glass.

10. An intraocular lens according to claim 1, wherein said lens portion is formed of polymeric material.

11. An intraocular lens adapted to be implanted in the eye comprising:
    a lens portion having a first portion and a second portion,
    said first portion including means for focusing light entering the eye,
    said second portion including means for deflecting light entering the eye away from the center of the retina; and
    means, coupled to said lens portion, for supporting said lens portion in the eye.

* * * * *